United States Patent [19]

Denton et al.

[11] Patent Number: 5,047,563

[45] Date of Patent: Sep. 10, 1991

[54] CHIRAL CROWN ETHERS

[75] Inventors: James B. Denton; Kin-Fai Yip, both of Elkhart, Ind.

[73] Assignee: Miles Inc., Elkhart, Ind.

[21] Appl. No.: 95,012

[22] Filed: Sep. 10, 1987

[51] Int. Cl.$^5$ ........................................... C07D 323/00
[52] U.S. Cl. ................................................. 549/353
[58] Field of Search ....................................... 549/353

[56] References Cited

U.S. PATENT DOCUMENTS 4,504,368  3/1985  Delton et al. .................. 549/353

OTHER PUBLICATIONS

Ikeda et al, "Synthesis of Ester Type Bis-12-Crown Ethers and their Complexing Abilities Toward Sodium Cation", Tetrahedron Lett., vol. 22, No. 37, pp. 3615-3616.

Primary Examiner—C. Warren Ivy
Assistant Examiner—Amelia A. Owens

[57] ABSTRACT

The synthesis and use of optically active isomers of bis(12-crown-4-methyl) dialkylmalonates as sodium specific ionophores is described. The synthesis of optically active isomers of hydroxymethyl 12-crown-4 useful in synthesizing ionophores is also described.

16 Claims, 2 Drawing Sheets

Meso-(R),(S)

3

Meso-(S),(R)

CHIRAL CROWN ETHERS

FIELD OF THE INVENTION

The present invention relates to chiral bis crown ethers. More specifically, the invention relates to the optically active isomers of bis (12-crown-4 methyl) dialkyl malonates and methods of preparing them. These chiral bis crown ethers are particularly useful as sodium specific ionophores. The invention also relates to optically active isomers of hydroxymethyl 12-crown-4 and methods for their preparation. These isomers are useful as intermediates for the preparation of ionophores.

BACKGROUND OF THE INVENTION

Introduction

The determination of aqueous ion concentrations has application in many fields such as water treatment and medicine. For example, the measurement of sodium and potassium levels in blood are important aids in diagnosis of numerous conditions.

The use of compounds and compositions which selectively isolate ions from a sample solution provide a variety of methods for measuring ion concentrations. These compounds, known as ionophores are capable of selectively forming a complex with a particular ion in an hydrophobic environment to the substantial exclusion of other ions. The use of ionophores has lead to five basic analytical approaches: ion selective electrodes, liquid/liquid partitioning, fluorescence enhancement, chromophore-labeled ionophore conjugates and test strips.

Ionophores include multidentate cyclic compounds which contain donor atoms in their cyclic chains. Such multidentate compounds can be mono- or polycyclic.

Monocyclic multidentate compounds which contain donor atoms which are electron rich and which are capable of complexing with particular cations are known as coronands. Typical coronands are crown ethers in which the monocyclic chain contains oxygen as the donor atom.

The polycyclic analogs of coronands are known as cryptands. Cryptands include bi- and tricyclic multidentate compounds. The cyclic arrangement of the donor atoms in cryptands is three dimensional and as a result, cryptands are capable of virtually surrounding a cation.

A third class of ionophores are known as podands. Podands are open chain ion specific compounds which, for example, contain a regular sequence of electron rich atoms such as oxygen.

Sodium Ionophores

A number of ionophores have been previously reported as useful in methods of detecting sodium. The tripodand, 1, 1, 1-tris [1, (2'-oxa-4'-oxo-5'-aza-5'-methyl) dodecanyl] propane has been found to be particularly useful for the determination of sodium ion. See U.S. Pat. No. 4,645,744 to Charlton et al. which is hereby incorporated by reference.

Other ionophores which have been reported to be useful for determining sodium include N, N'-dibenzyl-N, N'-dibenzyl-N, N'-diphenyl-1, 2-phenylenedioxydiacetamide, 6, 7, 9, 10, 18, 19-hexahydro-17-n-butyldibenzo [b, k] [1, 4, 7, 10, 13] pentaoxy-acyclohexadecane-18-yl-oxyacetic acid, and 15-crown-5.

Bis (12-crown-4-methyl) dodecylmethyl malonate has been reported to be a selective ionophore for sodium. Ikeda et al., Synthesis of Ester Type Bis-12-Crown-4 Ethers and Their Complexing Abilities Toward Sodium Cation, TETRAHEDRON LETTERS, vol. 22, no. 37, pp. 3615–16 (1981). Importantly, Ikeda and his co-workers state that the affect of stereo chemistry due to the presence of the chiral atoms on the 12-crown-4 ether rings will be small. The synthetic method disclosed in this reference yields only the isomeric mixture. The pure enantiomers and methods for their synthesis are not disclosed. Similarly, Japanese Patent No. 58-92852 discloses bis (12-crown-4) esters including dodecylmethyl malonate esters. The synthetic method disclosed yields only the isomeric mixture. The pure enantiomers and methods for their synthesis are not disclosed.

Synthesis of Hydroxymethyl 12-Crown-4 Ether and Bis (12-Crown-4 Methyl) Dialkyl Malonates The need for functional crown ethers for use in the synthesis of bis crown ethers has lead to several synthetic techniques for producing functional crown ethers. The synthesis of hydroxymethyl crown ethers starting from allyl glycidyl ether and oligoethylene glycols is disclosed in Ikeda et al. Facile Synthesis of Hydroxymethyl Crown Ethers, SYNTHESIS 73–76 (1984). Included among the synthetic techniques disclosed in this reference is the synthesis of hydroxymethyl 12-crown-4. Hydroxymethyl crown ethers, including hydroxymethyl 12-crown-4, can also be prepared by the intra molecular cyclization of the corresponding substituted oligoethylene glycols. Ikeda et al., Synthesis of Substituted Crown Ethers from Oligoethylene Glycols, JOURNAL OF ORGANIC CHEMISTRY, vol. 45, pp. 53, 55–58 (1980). All of these techniques produce the racemic mixture of hydroxymethyl 12-crown-4. The pure enantiomers and synthetic methods for producing them are not disclosed.

Methods of synthesis of bis (12-crown-4 methyl) dialkyl malonates are disclosed in Japanese patent 58-92852 and in Ikeda, TETRAHEDRON LETTERS 22, supra. The disclosed methods for preparing these esters start from the racemic mixture of hydroxymethyl 12-crown-4 and yield only the isomeric mixture of bis (12-crown-4 methyl) dialkyl malonates.

SUMMARY OF THE INVENTION

The present invention includes the pure enantiomers of hydroxymethyl 12-crown-4 and methods for preparing these enantiomers.

The invention is also directed to the optically active isomers of bis (12-crown-4 methyl) dialkyl malonates and methods for their synthesis.

In addition, both compositions and articles of manufacture comprising an optically active isomer of bis (12-crown-4 methyl) dialkyl malonate, a reporter substance and a hydrophobic carrier are within the scope of the invention.

DETAILED DESCRIPTION OF THE INVENTION

Definitions

As used herein, "substantially nonpolar" is intended as meaning that quality of a substance not to exhibit a substantial dipole moment or electrical polarity. In particular, it includes nonionic substances and substances which are dielectric.

The term "nonporous" is intended to mean substantially impervious to the flow of water. Thus, a nonporous carrier matrix is one which precludes the passage of water through it, one side to the other. For example, a polyvinyl chloride film would be considered for the purposes herein as being nonporous.

The expression "hydrophobic carrier" is used to describe the hydrophobic vehicle into which the ionophore and reporter substance are incorporated. As described below, the hydrophobic carrier can take the form of nonporous, nonpolar polymers, hydrophobic liquids and solids. The expression encompasses both the nonpolar, nonporous carrier matrix and the hydrophobic substance described below.

A "reporter substance" is one which is capable of interacting with an ionophore-ion complex to produce a color change or other detectable response. A preferred reporter for the determination of a cation is a neutral compound such as a dye capable of interacting with the ionophore-cation complex causing the reporter to lose a proton and become charged, affecting a change in electron distribution. The change in electron distribution produces a detectable response. The expression "reporter substance" includes phenolic compounds such as p-nitrophenol, which are relatively colorless in the non-ionized state but which color upon ionization, and fluorescent compounds which produce more or less fluorescence upon a change in electron distribution. The reporter substance can also be one which can trigger a detectable response together with other components. For example, the change in electron distribution in the reporter substance caused by interaction with the complex can in turn facilitate the interaction of the reporter with another component which would then produce a detectable response.

"Interacting" means any coaction between a reporter substance and an ionophore-ion complex which leads to a detectable response. An example of the reporter substance interacting with the complex is where the reporter is changed by the complex from a colorless to a colored state such as in the case of p-nitrophenol.

The expression "detectable response" is used to mean a change in, or occurrence of, a parameter in a test system which is capable of being perceived, either by direct observation or instrumentally, and which is a function of the presence of a specific ion in an aqueous test sample. Such detectable responses include the change in, or appearance of, color, fluorescence, reflectance, pH, chemiluminescence and infrared spectra.

The expression "lower alkyl", as used in the present disclosure, means an alkyl moiety containing about 1 to about 20 carbon atoms. Included in the meaning of lower alkyl are straight or branched chains, saturated or unsaturated, including methyl, ethyl, n-propyl, isopropyl, n-butyl, sec-butyl, tert-butyl and phenyl propyl. These can be unsubstituted or substituted, provided any such substituents not interfere with the operation of the test system.

By "pseudohalogen" is meant atoms or groups of atoms which, when attached to an unsaturated or aromatic ring system, affect the electrophilicity or nucleophilicity of the ring system, and/or have an ability to distribute an electrical charge through delocalization or resonance, in a fashion similar to the halogens. Thus, whereas halogen signifies Group VII atoms such as F, Cl, and I, pseudohalogens embrace such moieties as —CN, —SCN, —OCN, —$N_3$, —COR, —COOR, —CONHR, —$CF_3$, —$CCl_3$, —$NO_2$, —$SO_2CF_3$, —$SO_2CH_3$, and —$SO_2C_6H_4CH_3$, in which R is alkyl or aryl.

SYNTHESIS OF (S)(+)-HYDROXYMETHYL 12-CROWN-4

Generalized Synthetic Method

Figure 2:
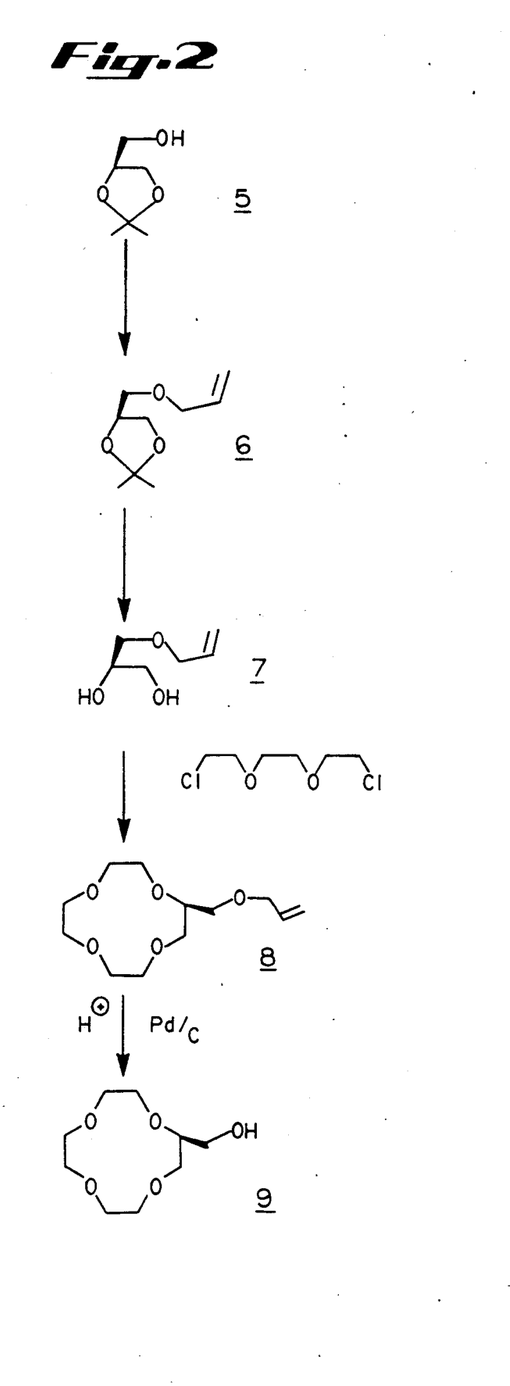
FIG. 2 illustrates a generalized reaction scheme for the synthesis of (S)(+)-hydroxy-methyl 12-crown-4.

The generalized reaction scheme for the preparation of (S)(+)-hydroxymethyl 12-crown-4 is shown in FIG. 2. (S)(+)-1-allyl-2,3-isopropylideneglycerol (6) is prepared by reacting (S)(+)-1,2-isopropylideneglycerol (5) with allyl bromide in the presence of alkaline base. (S)(+)-1-allyl-2,3-isopropylideneglycerol (6) is then isolated by filtration and distillation.

Compound 6 is then converted to (R)(+)-1-allylglycerol (7) by heating in the presence of inorganic acid. After neutralization, compound 7 is isolated and purified by filtration and distillation.

Compound 7 is then reacted with bis-chloroethoxyethane in the presence of lithium halide to form (R)(+)-allyloxylmethyl 12-crown-4 (8). The reaction mixture is neutralized and compound 8 is isolated by extraction and then purified by distillation.

Compound 8 is next treated with 10% palladium in carbon in the presence of acid to produce (S)(+)-hydroxymethyl 12-crown-4 (9). Compound 9 is then recovered by distillation.

EXAMPLE 1

Preparation of (S)(+)-1-Allyl-2,3-isopropylideneglycerol (6)

To a mixture of sodium hydroxide (12 g, 0.3 mole), potassium carbonate (10.7 g, 0.15 mole) and tributylammonium hydrogen sulfate (1.5 g) in 150 mL of toluene was added the (S)(+)-1,2-isopropylideneglycerol (5) (39.6 g, 0.3 mole) and allyl bromide (46.8 g, 0.36 mole). The mixture was stirred at room temperature for 30 min. and then at 80° C. for 5 hours. The mixture was cooled to room temperature. The insoluble solid was removed by filtration. The filtrate was concentrated and the oily residue was distilled under vacuum. A total of 42.4 g (80% yield) of 6 was recovered at 54°–56° C./5mm.

Analysis: Calculated for $C_9H_{16}O_3$: C, 62.76; H, 9.36.
PMR (60 MHz, $CDCl_3$)δ: 1.38 (s, 3H, —$CH_3$); 1.45 (s, 3H, —$CH_3$); 3.48–4.40 (m, 7H), 5.10–6.30 (m, 3H, allyl).
IR ($CHCl_3$ cm$^{-1}$): 3000, 2880, 1380, 1230, 1080.
Mass. Spect. (CI): (m+1)=173.
$\alpha_{Na}$ = +21.4 (neat).

(R)(+)-1-Allylglycerol(7)

Compound 6 (40 g, 0.23 mole) was mixed with 30 mL of acetone and 90 mL of 1.0N HCl. The mixture was heated on a stream bath for 30 min. After the acetone was removed from the mixture by evaporation, the pH of the solution was adjusted to 7.0 with concentrated KOH. Water was then removed by evaporation. The residue was mixed with 100 mL of ether. The precipitate was removed by filtration. After the ether was evaporated from the filtrate, the oil was distilled under vacuum. The product (28.5 g oil, yield 93%) was recovered at 78°-85° C./0.5 mm.

Analysis: Calculated for $C_6H_{12}O_3$: C, 54.53; H, 9.16. Found: C, 43.77; H, 9.32.

PMR (60 MHz, $CDCl_3$) δ: 3.50-4.10 (m, 9H); 5.10-6.30 (m, 3H, allyl).

IR ($CHCl_3$) $cm^{-1}$: 3400, 3000, 2860, 1080, 940.

Mass Spect. (CI): (M+1)=133.

$\alpha Na = +5.84$ (neat).

(R)(+)-Allyloxylmethyl 12-crown-4 (8)

Lithium metal (4 g, 0.57 mole) was refluxed with 1,000 mL of t-butanol under anhydrous conditions overnight. After the solution was cooled to room temperature, lithium bromide (17.4 g, 0.2 mole), compound 7 (26.4 g, 0.2 mole), bis-chloroethoxyethane (38.57 g., 0.2 mole) and water (3.56 mL) were added. The mixture was heated at 100° C. for one week. After the reaction, solvents were removed by evaporation. Ice (200 g) was then added. After all the solid was dissolved, the pH of the solution was adjusted to 7.0 with 5N HCl. The mixture was extracted with ether. The ether solution was dried over anhydrous $Na_2SO_4$ and evaporated to an oil which was then purified by distillation under vacuum. Compound 8 (28.2 g oil, 57% yield) was recovered at 85°-110° C./0.1 mm.

Analysis Calculated for $C_{12}H_{22}O_5$: C, 58.52; H, 9.00. Found: C, 57.90; H, 8.88 pMR (60 MHz, $CDCl_3$) δ: 3.40-4.05 (m, 19H, —$OCH_2$—), 5.10-6.30 (m, 3H, allyl).

IR ($CHCl_3$) $cm^{-1}$: 3000, 2910, 2860, 1130.

Mass. Spect. (FAB): (m+1)=247.

$\alpha Na = +27.7$ (neat).

(S)(+)-Hydroxymethyl 12-crown-4 (9)

Compound 8 (26 g, 106 moles) was dissolved in 100 mL of 50% ethanol. The solution was treated with 10% Pd in carbon (2.5 g) and p-toluenesulfonic acid (1 g.). The mixture was stirred at 80° C. overnight. The solid was then removed by filtration. After the ethanol in the filtrate was removed by evaporation, 200 mL water was added and the solution was washed with 2×100 mL of ether. The pH of the solution was adjusted to 7.0 with concentrated NaOH. The solution was then evaporated and the residue distilled under vacuum. Compound 9 (18.1 g oil, 83% yield) was recovered at 115°-120° C./0.1 mm.

Analysis: Calculated for $C_9H_{18}O_5$: C, 52.42; H, 8.80. Found: C, 52.05; H, 8.85.

PMR (60MHz, $CDCl_3$) δ: 3.00 (broad s, 1H, OH), 3.65-3.90 (m, 17H, —$OCH_2$)

IR ($CHCl_3$) $cm^{-1}$: 3400, 3000, 2910, 2860, 1140.

Mass. Spect. (FAB): (m+1)=207.

$\alpha Na = +31.9$ (neat)

SYNTHESIS OF (R)(−)-HYDROXYMETHYL 12-CROWN-4

Figure 3:
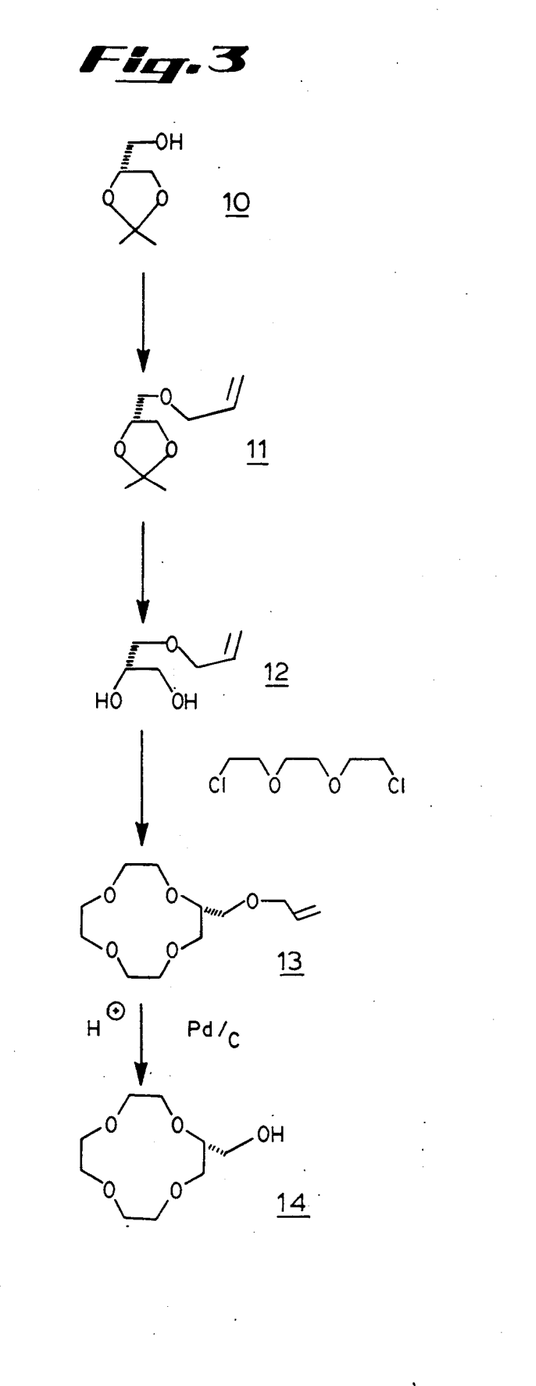
FIG. 3 illustrates a generalized reaction scheme for the synthesis of (R)(-)-hydroxymethyl 12-crown-4.

Generalized Synthetic Method (R)(−)-hydroxymethyl 12-crown-4, with the exception of the starting material, is prepared by the same technique as just described for (S)(+)-hydroxymethyl 12-crown-4. To prepare the (R)(+) isomer, the synthesis is begun using (R)(-)-1, 2-isopropylideneglycerol.

EXAMPLE 2

Synthesis of (R)(−)-Hydroxymethyl 12-Crown-4

(R)(−)-1-Allyl-2,3-isopropylideneglycerol (11).

To a mixture of sodium hydroxide (4 g, 0.1 mole), potassium carbonate (6.9 g, 0.05 mole) and tributylammonium hydrogen sulfate (0.5 g) in 50 mL of toluene was added the (R)(−)-1,2-isopropylideneglycerol (10) (13.5 g, 0.2 mole) and allyl bromide (15.6 g, 0.12 mole). The mixture was stirred at room temperature for 30 min. and then at 80° C. for 5 hrs. The mixture was cooled to room temperature. The insoluble solid was removed by filtration. The filtrate was concentrated and the oily residue was distilled under vacuum. A total of 14 g (80% yield) of 11 was recovered at 54°-56° C./5mm.

PMR (60 MHz, $CDCl_3$) δ: 1.38 (s, 3H, —$CH_3$); 1.45 (s, 3H, —$CH_3$); 3.48—4.40 (m, 7H), 5.10-6.30 (m, 3H, allyl).

IR ($CHCl_3$) $cm^{-1}$: 3000, 2880, 1380, 1230, 1080.

Mass. Spect. (CI): (m+1)=173.

$\alpha Na_{Na} = -20.4$ (neat).

(S)(−)-1-Allylglycerol (12)

Compound 11 (13.5 g, 78 moles) was mixed with 10 mL of acetone and 30 mL of 1.0N HCl. The mixture was heated on a steam bath for 30 min. After the acetone was removed from the mixture by evaporation, the pH of the solution was adjusted to 7.0 with concentrated KOH. Water was then removed by evaporation. The residue was mixed with 100 mL of ether. The precipitate was removed by filtration. After the ether was evaporated from the filtrate, the oil was distilled under vacuum. The product (8.0 g oil, yield 78%) was recovered at 78°-85° C./0.5 mm.

Analysis: Calculated for $C_6H_{12}O_3$: C, 54.53; H, 9.16. Found C, 54.88; H, 8.86.

PMR (60 MHz, $CDCl_3$) δ: 3.50-4.10 (m, 9H); 5.10-6.30 (m, 3H, allyl).

IR ($CHCl_3$) $cm^{-1}$: 3400, 3000, 2860, 1080, 940.

Mass. Spect. (CI): (m+1)=133.

$\alpha_{na} = -5.49$ (neat).

(S)(−)-Allyloxymethyl 12-crown-4 (13)

Lithium metal (1.2 g, 0.17 mole) was refluxed with 300 mL of t-butanol under anhydrous conditions overnight. After the solution was cooled to room temperature, lithium bromide (5.22 g, 60 moles), compound 12 (7.92 g, 60 moles), bis-chloroethoxyethane (11.5 g, 60 moles) and water (1 mL) were added. The mixture was heated at 100° C. for one week. After the reaction, solvents were removed by evaporation. Ice (100 g) was then added. After all the solid was dissolved, the pH of the solution was adjusted to 7.0 with 5N HCl. The mixture was extracted with ether. The ether solution was dried over anhydrous $Na_2SO_4$ and evaporated to an oil which was then purified by distillation under vacuum. Compound 8 (8.0 g oil, 54% yield) was recovered at 85°-110° C./0.1 mm.

PMR (60 MHz, $CDCl_3$) δ: 3.40-4.05 (m, 19H, —$OCH_2$—), 5.10-6.30 (m, 3H, allyl).

IR ($CHCl_3$) $cm^{-1}$: 3000, 2910, 2860, 1130. Mass. Spect. (FAB): (m+1)=247.

$\alpha_{Na} = -25.0$ (neat).

(R)(−)-Hydroxymethyl 12-crown-4 (14).

Compound 13 (8.0 g, 32.5 moles) was dissolved in 40 mL of 50% ethanol. The solution was treated with 10% Pd in carbon (1 g) and p-toluenesulfonic acid (0.4 g). the mixture was stirred at 80° C. overnight. The solid was then removed by filtration. After the ethanol in the filtrate was removed by evaporation, 100 mL water was added and the solution was washed with 2×100 mL of ether. The pH of the solution was adjusted to 7.0 with concentrated NaOH. The solution was then evaporated and the residue distilled under vacuum. Compound 14

(5.0 g oil, 76% yield) was recovered at 115°–117° C./0.1 mm.

PMR (60 MHz, CDCl$_3$) δ: 3.00 (broad s, 1H, OH), 3.65–3.90 (m, 17H).

IR (CHCl$_3$) cm$^{-1}$: 3400, 3000, 2910, 2860, 1140.

Mass. Spect. (FAB): (m+1)=207.

αNa= −26.7 (neat).

Synthesis of Chiral Bis (12-Crown-4 Methyl) Dialkyl Malonates

Utilizing the hydroxymethyl 12-crown-4 enantiomers prepared by the above methods, the chiral bis (12-crown-4 methyl) dialkyl malonates can be prepared. The esters can be prepared from dialkyl malonic acid, dialkyl malonates or dialkyl malonyl dichloride. The general structure of the malonic compound can be represented as where X is Cl, OH or OR$_3$, R$_3$ is lower alkyl of 1–4 carbon atoms, R$_1$ is methyl and R$_2$ is alkyl of 4–20 carbon atoms.

For example, utilizing appropriate catalysts, the bis crown ether can be prepared starting with a dialkyl malonic acid. The preferred starting material is a dialkyl malonyl dichloride. Irrespective of which starting material is chosen, one of ordinary skill in the art will recognize the need for an appropriate catalyst to facilitate formation of the ester.

Figure 1:
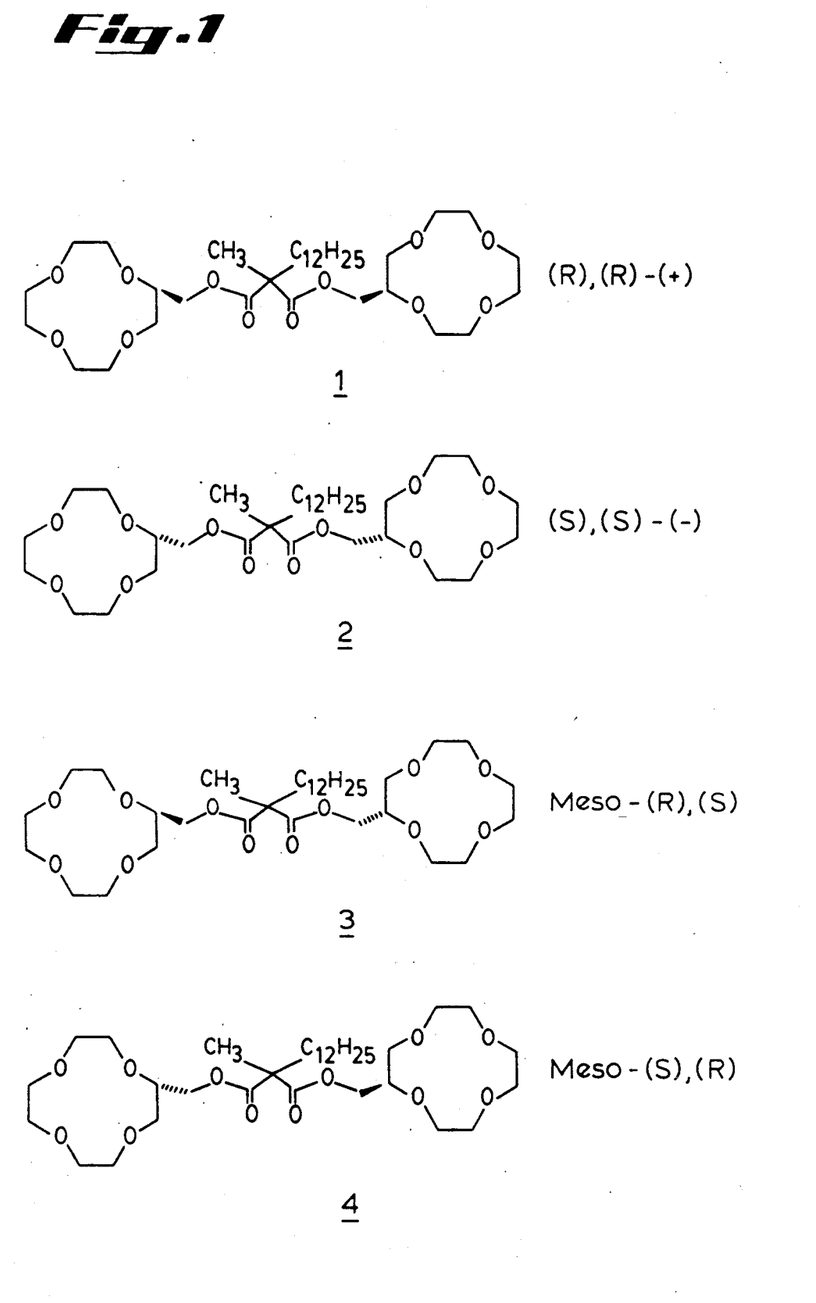
FIG. 1 illustrates the four stereo isomers of bis (12-crown-4 methyl) dodecylmethyl malonate.

The best performance as a sodium ionophore has been found when the malonate is disubstituted with a methyl group and an alkyl group of about 4 to about 20 carbon atoms. The preferred ionophores are (R)(R)-(+) bis (12-crown-4 methyl) dodecylmethyl malonate (1), (S)(S)-(−) bis (12-crown-4 methyl) dodecylmethyl malonate (2) and mixtures of the two compounds. FIG. 1 depicts the structure of compounds 1 and 2 as well as the structure of meso-(R),(S)-bis (12-crown-4 methyl) dodecylmethyl malonate (3) and meso-(S),(R)-bis (12-crown-4 methyl) dodecylmethyl malonate (4). As will be shown below, compounds 1 and 2 or a mixture of compounds of 1 and 2 were surprisingly found to give the best performance as sodium ionophores when compared to mixtures of compounds 3 and 4 or a mixture of compounds 1, 2, 3 and 4.

EXAMPLE 3

Synthesis of (R),(R)-(+)Bis(12-Crown-4-Methyl)Dodecylmethyl Malonate (1)

To a cold solution (−30° C.) of compound 9 (6.18 g, 30 moles) and triethylamine (3.35 g, 33 moles) in 80 mL of methylene chloride, dodecylmethylmalonyl dichloride (4.28 g, 12 moles) was added. The mixture was stirred at room temperature for two hours and then at 40° C. for three days. After the reaction, solvent was removed by evaporation. The residue was mixed with 100 mL of ether and the precipitate was removed by filtration. The filtrate was concentrated and then purified by 500 g of silica gel flash column using 2% methanol in chloroform as solvent. Fractions containing the desired product were pooled and evaporated to give 3.2 g (40%) of 1.

Analysis: Calculated for C$_{34}$H$_{62}$O$_{12}$: C, 61.60; H, 9.43.

Found: C, 61.68; H, 9.22.

PMR (60 MHz, CDCl$_3$) δ: 0.90 (5, 3H, —CH$_3$), 1.30 (s, 22H, —CH$_2$—), 1.45 (s, 3H, —CH$_3$), 3.60–4.20 (m, 17H, —OCH$_2$).

IR (CHCl$_3$) cm$^{-1}$: 3000, 2910, 2850, 1730, 1460, 1240, 1120.

Mass. Spect. (FAB): (m+Na)=685.

[α]$_{Na}$= +12.2 in methylene chloride (c=3.06).

EXAMPLE 4

Synthesis of (S),(S)-(−)Bis(12-Crown-4-Methyl)Dodecylmethyl Malonate (2)

To a cold solution (−30° C.) of compound 14 (2.06 g, 10 moles) and triethylamine (1.12 g, 11 moles) in 25 mL of methylene chloride, dodecylmethylmalonyl dichloride (1.78 g, 5 moles) was added. The mixture was stirred at room temperature for two hours and then at 40° C. for three days. After the reaction, solvent was removed by evaporation. The residue was mixed with 100 mL of ether and the precipitate was removed by filtration. The filtrate was concentrated and then purified by 200 g of silica gel flash column using 2% methanol in chloroform as solvent. Fractions containing the desired product were pooled and evaporated to give 0.85 g (26%) of 1.

Analysis Calculated for C$_{34}$H$_{62}$O$_{12}$: C, 61.60; H, 9.43.H

Found: C, 62.07; H, 9.46.

PMR (60 MHz, CDCl$_3$) δ: 0.90 (t, 3H, —CH$_3$), 1.30 (s, 22H, —CH$_2$—), 1.45 (s, 3H, —CH$_3$), 3.60–4.20 (m, 17H, —OCH$_2$—).

IR (CHCl$_3$) cm$^{-1}$: 3000, 2910, 2850, 1730, 1460, 1240, 1120.

Mass. Spect. (FAB): (m+Na)=685.

[α]$_{Na}$= −12.0 in methylene chloride (c=2.34).

EXAMPLE 5

Synthesis of Mixture of Meso-(R),(S)-Bis(12-Crown-4-Methyl)Dodecylmethyl Malonate (3) and Meso-(S),(R)-Bis(12-Crown-4-Methyl)Dodecylmethyl Malonate (4)

To a cold solution (−30° C.) of compound 9 (1.03 g, 5 moles) and triethylamine (0.56 g. 5.5 moles) in 25 mL of methylene chloride, dodecylmethylmalonyl dichloride (1.78 g, 5 moles) was added. The mixture was stirred at room temperature overnight. Compound 14 (1.03 g, 5 moles) and more triethylamine (0.56 g, 5.5 moles) were then added. The mixture was heated at 40° C. for two days. After the reaction, solvent was removed by evaporation. The residue was mixed with 40 mL of ether and the precipitate was removed by filtration. The filtrate was concentrated and then purified by 200 g of silica gel flash column using hexane-acetone as solvent. Fractions containing the desired product were pooled and evaporated to give 0.8 g (24%) of a mixture of 3 and 4.

Analysis: Calculated for C$_{34}$H$_{62}$O$_{12}$: C, 61.60; H, 9.43.

Found: C, 61.36; H, 9.56

PMR (60 MHz, CDCl$_3$) δ: 0.90 (t, 3H, —CH$_3$), 1.30 (s, 22H, —CH$_2$—), 1.45 (s, 3H, —CH$_3$), 3.60–4.20 (m, 17H, —OCH$_2$—).

IR (CHCl$_3$r) cm$^{-1}$: 3000, 2910, 2850, 1730, 1460, 1240, 1120.

Mass. Spect. (FAB): (m+Na)=685.

[α]$_{Na}$=0 in methylene chloride (c=2.14).

TEST METHODS

The novel ionophores described above can be used in techniques utilizing ion selective electrodes, liquid/liquid partitioning, fluorescence enhancement, chromophore labeled ionophore-conjugates and test strips. The following discussion is illustrative of the ionophores use in test strips to determine sodium concentrations.

Test Strips

The ionophores of the present invention are well adapted for use in a test system comprising the ionophore and a reporter substance both incorporated into a hydrophobic carrier. Such a system can, for example, be impregnated into paper or mounted on a support to form test strips. Sodium, in an aqueous sample, can enter the matrix and complex with the ionophore. The ion-ionophore complex interacts with the reporter substance producing a detectable response.

Test strips utilizing the present invention can take the form of those described in U.S. Pat. No. 4,645,744 wherein a test means comprising the ionophore and the reporter substance is incorporated into a substantially nonpolar, nonporous carrier matrix. Alternatively, the test strip can take the form of a porous support matrix impregnated with a homogeneous hydrophobic composition containing the ionophore and reporter substance. Such test strips are described in U.S. Pat. No. 4,670,218, assigned to the present assignee and which is hereby incorporated by reference. The porous support matrix referred to herein is the same as porous carrier matrix described in that application.

Nonionic And Water Insoluble

The carrier matrix is fabricated from a non-ionic, water insoluble material. These materials all exhibit the property of being hydrophobic. Examples of such materials are films of polymers such as polyvinyl fluoride, polyvinyl chloride, vinyl chloride/vinyl acetate copolymer, vinyl chloride/vinylidene chloride copolymer, vinyl chloride/vinyl acetate/vinyl alcohol terpolymer, vinylidine chloride/acrylonitrile copolymer, polyacrylates, polymethacrylates, and polyurethanes. Additional hydrophobic polymeric materials such as silicone polymers are also suitable for use as the carrier matrix.

The carrier matrix must be of a material which precludes substantial penetration of the matrix by the aqueous test sample. Both the ionophore and the reporter substance should be substantially insoluble in the aqueous test sample due to their being entrapped within the carrier matrix. The requirement of nonporosity of the carrier matrix precludes substantial dissolution or leaching of the ionophore or the reporter substance and prevents permeation of the test system by sample components other than the ionic analyte.

The test system, i.e., the ionophore, the reporter substance and the carrier matrix can also be dispersed in a hydrophyllic material such as gelatin, agarose, poly(vinyl alcohol), poly(propylene imine), carrageenan, and alginic acid. These water soluble or water wettable polymers in their dry state exhibit a marked wetability by aqueous media. In such a case, in addition to the carrier matrix materials previously listed, the ionophore and reporter substance could also be dissolved in a hydrophobic liquid. Such a liquid must be relatively non-volatile, i.e., having a boiling point of at least about 150° C. Typical liquids which fall into this category are tricresylphosphate, 2-nitrophenyloctyl ether, 2-nitrophenylbutyl ether, dioctylphthalate, tris-2-ethylhexyl phosphate, di-2-ethylhexyl sebacate, and n-butyl acetyl ricinolate.

Porous Support Matrix

Alternatively, the test strip can be prepared by impregnating a hydrophobic composition containing the ionophore and reporter substances into a porous support matrix. The support matrix with which the homogeneous hydrophobic composition is incorporated must be able to support a hydrophobic phase in such a way that substantial openings exist after drying into which an aqueous test sample can easily move, i.e., it must be porous.

Suitable materials include paper, wood, and other cellulosic systems, sintered ceramic frits, and porous polymeric materials provided that the dimensional integrity of the matrix is maintained upon incorporation of the hydrophobic composition and subsequent contact with an aqueous sample. In addition, the matrix material cannot interact with the hydrophobic composition in a way which would interfere with the production of a detectable response.

A preferred support matrix is paper. For example, filter paper can be incorporated with a homogeneous hydrophobic composition and dried. The paper can also be incorporated with a buffering substance. Upon contacting the test means with an aqueous test sample, the ion can easily reach the hydrophobic phase by flowing into the open lattice of the paper. Since the buffer is incorporated directly with the test means, no sample dilution is necessary to provide the proper pH.

Hydrophobic Substance

The primary function of the hydrophobic substance, also referred to as a hydrophobic carrier, is to increase the detectable response of the test means by isolating the ionophore and the reporter from the aqueous phase produced by contact with the test sample. In this respect, its function is the same as that of the nonporous carrier matrix described above. Thus, the substance can be a liquid, a solid or combination thereof, provided that it increases the ability of the ionophore-ion complex and reporter substance to coexist in the homogeneous hydrophobic composition. It is speculated that the hydrophobic substance interacts with the ionophore-ion complex in such a way as to overcome the natural tendency of charged ions to prefer an aqueous phase and in some way stabilizes the complex when formed in the hydrophobic composition. Care must be exercised to choose a substance or combination of components to act as the hydrophobic substance which does not interfere with the interaction of the complex and the reporter. However, given the present disclosure, one knowledgeable in the art will be able to choose from many compounds, or combinations thereof, which will provide a suitable hydrophobic substance.

Substances which are useful as the hydrophobic carrier include liquids which are capable of dissolving both the ionophore and the reporter. Because a liquid could dissolve, or be leached out, into the aqueous test sample, it is preferable that the liquid be relatively insoluble in the test sample of interest.

Preferred liquids are relatively nonvolatile, i.e., have a boiling point of at least about 150° C., ideally at least about 200° C. Such liquids are normally oxygen donors, containing functional groups such as ether, ester, amide and the like or combinations thereof.

Typical liquids which fall into this category are tricresylphosphate, dioctylphthalate, tris-2-ethylhexylphosphate, di-2-ethylhexyl sebacate, n-butylacetylricinolate and nitrophenyl ethers such as 2-nitrophenyl octyl ether, 2-nitrophenyl butyl ether, dibenzyl ether and o-nitrophenyl-2-(1,3,3)-trymethyl-butyl-5,7,7-tryethyl octyl ether. Mixtures of these liquids can be used. 2-nitro-phenyl octyl ether is preferred.

Useful solids include cellulose acetate, cellulose propionate, and polymers such as styrene/maleic anhydride copolymer, vinylidene chloride/acrylonitrile copolymer, styrene/allyl alcohol copolymer and poly(methyl methacrylate). Other useful polymers are poly(vinyl chloride), poly(vinylidene fluoride), polystyrene, polycarbonate, poly(4-chlorostyrene), poly(vinyl acetate), vinylidene chloride/vinyl chloride copolymer, vinyl chloride/vinyl acetate copolymer, vinyl chloride/vinyl acetate/vinyl alcohol terpolymer, polyethylene, polypropylene and polyurethane. Polymethylmethacrylate is preferred. Of course many other polymeric materials are suitable for use. The identification of such materials is well within the skill of the art, given the present disclosure.

It is possible to obtain formulations with sufficient sensitivity to produce a clinically useful ion test system using only a high boiling liquid as the hydrophobic substance, using only a solid hydrophobic substance or using a combination of such components. For example, a working formulation for a sodium test means can be produced using a homogeneous hydrophobic composition containing the optically active ionophores, previously described, a reporter substance and a polymeric solid as the hydrophobic carrier. In some formulations, the combination of a polymer and a high boiling liquid can improve the response of the system so that a visual determination can be correlated semiquantitatively with ion concentrations.

Reporter Substances

Given the presence of the ion of interest (sodium) in the test solution, it is the reporter substance which provides the detectable response as a result of its interacting with the ionophore/ion complex. The reporter substance can range in composition from a single compound which can ionize in response to the formation of the ionophore/ion complex, to a mixture of reactive species which produce a detectable product when their reaction chain is triggered by the complex. Thus it can be seen that when no ion-analyte is present, the reporter substance remains inactive and no detectable response is observed. Alternatively, when the particular ion of interest is present, it is enabled by the ionophore to enter the carrier matrix to form a complex. This complex interacts with the reporter substance and induces it to undergo a detectable change.

In the case where the reporter is a single compound, it can include a dissociable group such that upon dissociation the ionic species formed exhibits a color different from the undissociated species. For the determination of cations such as sodium, particularly preferred reporters are neutral compounds having dissociable protons such that upon interaction of the ionophore-cation complex with the reporter, the reporter loses a proton. This proton loss causes a change in, or appearance of, a detectable response in the matrix. Tetrabromophenolphthalein alkyl esters are useful reporters. Phenolic compounds such as p-nitrophenol, which are relatively colorless in the nonionized state but are colored upon ionization are also useful. Other compounds, such as those which produce more or less fluorescence upon a change in the electron distribution, can also be used. Classes of fluorescent indicators and their derivatives which are useful in this invention included derivatives of fluorescein, especially fluorescein esters, 7-hydroxy coumarins, resorufins, pyrene-3-ols and flavones.

The reporter substance can also be one which can trigger a detectable response together with other components. For example, a reaction sequence useful as the reporter substance is one which involves the dissociation of a proton to a phenol, thus initiating a coupling reaction to form a colored product. The so-called Gibbs reaction is typical of such a reaction sequence in which 2,5-cyclohexadiene-1-one-2,6-dihalo-4-haloimine couples with a phenol to form a colored reaction product. A more detailed description of this and other reporter substances and their chemistry can be found in U.S. Pat. No. 4,645,744 previously incorporated by reference.

The preferred reporter substance is a compound having the structure in which R* is an intermediate alkyl group, i.e., having 5–15 carbon atoms, in which R' is H or lower alkyl of 1 to 7 carbon atoms and X is halogen or pseudohalogen. Compounds such as these have been found to be especially resistant to possible interference due to the presence of serum albumin in the test sample. The most preferred reporter substance is a compound of this type in which R* is n-decyl, X is a chloro group and R' is methyl. This compound, 7-(n-decyl)-2-methyl-4-(3', 5' dichlorophen-4'-one) indonaphthol will be referred to hereinafter as 7-decyl-MEDPIN. Additional information on the preparation and use of such compounds can be found in U.S. Pat. No. 4,552,697, which is hereby incorporated by reference.

Optional Components

The test system can optionally include photochemical stabilizers, thickeners, preservatives and so forth, provided they do not interfere with the production of the detectable response. Given the present disclosure, the choice of such components is well within the skill of those knowledgeable in the art.

Concentration Ranges of Test System Components

The concentration of the test system components are not critical to the invention provided that the concentrations of the ionophore and reporter substance are sufficient to produce the desired detectable response. For qualitative results, neither the concentration of the ionophore nor the concentration of the reporter substance is tied to the concentration range of the ion-analyte to be determined.

Determination of optimum concentrations is within the ability of one skilled in the art, given the present disclosure. However, the following guidelines are provided. It is preferred that the ionophore be present in molar excess over the reporter substance (i.e., greater than 1:1 molar ratio, ionophore : reporter substance). Working concentrations of the ionophore can range from 2 gm/l to saturation.

The working and preferred concentration ranges for a test means responsive to sodium ion are given below. Preferred ranges are given for the determination of serum sodium by reflectance on an Ames Seralyzer ® reflectance photometer.

| Reagent | Working Concentration | Preferred Concentration |
|---|---|---|
| Hydrophobic Mixture (concentration given in gm/L of Organic Solvent) | | |
| Ionophore | 2-200 gm/L (3-300 mm) | 5-30 gm/L (7.5-4.5 mm) |
| Reporter | 0.5-50 gm/L (1-100 mm) | 1.5-6 gm/L (3-13 mm) |
| Hydrophobic polymer | 0.01-50 gm/L | 0.02-30 gm/L |
| Buffer Mixture (concentrations given relate grams to concentration per L of water or water-miscible solvent) | | |
| Buffer | 0.1-1.0 M | 0.1-0.8 M |

Test Device

The test system described above can be used by itself, prepared in a multi-layer format and/or mounted at one end of an elongated support member In addition, the test system can be incorporated into an absorbent material such as filter paper. A preferred type of filter paper is quantitative filter paper which has sufficiently high purity to enable its use in quantitative analytical techniques such as gravimetric analysis. A detailed discussion of single and multi-layer supported test devices is found in U.S. Pat. No. 4,645,744. A detailed discussion of test devices using a porous carrier such as paper is found in U.S. Pat. No. 4,670,218. The ionophore of this invention is suitable for incorporating into such test devices as described in these references.

Preparation of Sodium Reagent Strips

Test strips incorporating the novel ionophores of this invention can be prepared by impregnating paper with a test system as defined above. A suitable porous carrier matrix such as paper is impregnated with a solution of the ionophore, reporter substance and hydrophobic substance or carrier. The solvent used should be sufficiently volatile to allow its removal following impregnation. Suitable solvents include toluene, xylene, methyl ethyl ketone, tetrahydrofuran, n-butyl acetate, acetone, ethylene glycol monomethyl ether, etc. After impregnation, the paper is dried at a temperature sufficient to remove the solvent.

A buffer or combination of buffers should also be incorporated with the paper. After the solvent removal just described is completed, the paper is impregnated with a second solution containing an appropriate buffer or buffers. Upon contact with an aqueous fluid sample, the buffer redissolves into the aqueous phase thus created, raising or lowering the pH to the desired level for the generation of the detectable response to proceed. With preferred reporters capable of losing a dissociable proton upon interaction with the ionophore-ion complex, the buffer maintains a suitable pH for the reaction to proceed. Prebuffering allows the test device to be used with unbuffered and undiluted samples such as serum or whole blood.

Suitable buffers include bis[2-hydroxyethyl] imino-tris[hydroxymethyl] methane, 1,3-bis[tris(hydroxymethyl) methyl amino]propane, N,N-bis-(2 hydroxyethyl) glycine, tris(hydroxymethyl)aminomethane, N-ethyl) [2-acetamido]2-iminodiacetic acid, N-2-hydroxyethyl-piperazine-N', 3-propane sulfonic acid, 3[N-tris(hydroxymethyl)methyl amino-2-hydroxy propane] sulfonic acid; tetramethylammonium borate, 3-[cyclohexylamino)-propane sulfonic acid and tetralmethylammonium phosphate. Bis[2-hydroxyethyl] imino- tris[hydroxymethyl] methane is preferred.

The preferred pH range depends on the reporter substance. Therefore, the choice of the buffer is determined by the reporter substance used and to some extent by the desired detectable response. For example, when 7-decyl-MEDPIN is used as the reporter, the preferred pH range is from 6-8.5. However, when a reporter substance having a higher pKa for the dissociable proton is used, a higher pH range will be preferred. Similarly, when a reporter having a lower pKa for a dissociable proton as used, a lower pH range will be preferred. When the detectable response is a color change, the buffer can influence the degree of such detectable response, and the particular buffer can be chosen for color intensity optimization. For example, the useful pH range for the reporter, 7-decyl-MEDPIN occurs from about pH 6-8.5 where the color changes from orange to blue. A higher pH, pH 8.5-10, gives shades of dark blue which are difficult to distinguish visually, and a lower pH, pH 5-6 gives shades of pale yellow, also difficult to distinguish visually. Both pH extremes could be used with instrumental analysis, although the best instrumental precision occurs at the pH range of from about 6-8.5. Determination of a suitable pH is a routine laboratory experiment.

EXAMPLE 6

Preparation of Sodium Reagent Strips

Whatman 31ET paper was impregnated with two solutions and dried at 60° C. after saturation with each solution.

First Solution
- 15 mL : toluene
- 0.15 g : polymethylmethacrylate (DuPont Elvacite 2010)
- 0.3 g : bis(12-crown-4) isomer
- 75 mg : 7-decyl-MEDPIN Second Solution:
- 10.5 g Bis-tris [Bis (2-hydroxyethyl) imino-tris-(hydroxy-methyl) methane]
- Phosphoric acid to adjust pH to 6.4 quantity sufficient to provide 100 mL

EXAMPLE 7

Determination of Cation Selectivity

The dry papers were reacted with 30 L of an aqueous salt solution or 30 L of 1:3 diluted serum. The aqueous concentrations were 0, 25, 45, 65 and 85 mM NaCl; 400, 600, 800 and 1000 mM LiCl; 200, 400, 600 and 800 mM KCl. The serum samples with concentrations 127.4, 152.8, 178.5, 204.2 and 229.8 mM NaCl, were diluted 1:3 with water. The reflectance was measured at 640 nm between 40 and 60 seconds with the Seralyzer ® reflectance photometer. The K/S values, which were computed from the average reflectance readings, were plotted versus concentration The slopes of the K/S versus concentration plot are reported in the following table.

| Isomer | Aqueous Samples | | | | | 1:3 Diluted Serum $(mM^{-1})$ Slope |
|---|---|---|---|---|---|---|
| | $(mM^{-1})$ NaCl Samples Slope | $(mM^{-1})$ KCl Samples Slope × $10^4$ | Slope (NaCl)/ Slope (KCl) | $(mM^{-1})$ LiCl Samples Slope × $10^5$ | Slope (NaCl)/ Slope (LiCl) | |
| (R)(R)(+) | 0.0317 | 5.39 | 58.8 | 3.48 | 911 | 0.0118 |
| (S)(S)(−) | 0.0341 | 5.72 | 59.6 | 3.71 | 919 | 0.0125 |
| (R)(S) & (S)(R) | 0.0139 | 5.08 | 27.4 | 4.64 | 300 | 0.00413 |
| (R)(R)(+) & (S)(S)(−) | 0.0307 | 5.32 | 57.7 | 3.70 | 830 | 0.0105 |
| Racemic Mixture | 0.0207 | 4.23 | 48.9 | 2.80 | 739 | 0.00735 |

The above data demonstrates that in terms of selectivity for sodium over that for potassium or lithium that both the (R)(R)(+), the (S)(S)(−) isomers and the mixture thereof are superior to either the racemic mixture or the mixture of the two meso isomers. The quantity slope(NaCl)/slope(KCl) is a measure of the selectivity for sodium over that for potassium. The data also shows that for these optically active isomers, the selectivity for sodium is sufficiently high that any contribution by potassium or lithium ions in the sample can be ignored.

In general, the data demonstrates that a highly sodium specific test system can be devised using the novel ionophores of this invention. The high degree of selectivity is all the more surprising in view of the prediction of the prior art that the effect of stereo chemistry would be small.

Obviously, many other modifications and variations of the invention as hereinbefore set forth may be made without departing from the spirit and scope thereof.

WHAT IS CLAIMED:

1. A composition comprising an ionophore selected from optically active isomers of bis (12-crown-4 methyl) dialkyl malonates, wherein one alkyl group is methyl and the second alkyl group has from 4 to 20 carbon atoms.

2. The composition of claim 1 wherein said isomer is (R),(R)-(+) bis (12-crown-4 methyl) dialkyl malonate.

3. The composition of claim 2 wherein said isomer is (R),(R)-(+) bis (12-crown-4 methyl) dodecylmethyl malonate.

4. The composition of claim 1 wherein said isomer is (S),(S)-(−) bis (12-crown-4 methyl) dialkyl malonate.

5. The composition of claim 4 wherein said isomer is (S),(S)-(−) bis (12-crown-4 methyl) dodecylmethyl malonate.

6. A composition comprising an ionophore selected from the group of (R),(R)-(+) bis (12-crown-4 methyl) dodecylmethyl malonate, (S),(S)-(−) bis (12-crown-4 methyl) dodecylmethyl malonate and mixtures thereof.

7. A method of preparing optically active bis (12-crown-4 methyl) dialkyl malonates comprising reacting a compound selected from
(S)(+)-hydroxymethyl 12-crown-4 and
(R)(−)-hydroxymethyl 12-crown-4 with
a compound having the general formula wherein X is Cl, OH or $OR_3$ and $R_3$ is lower alkyl of 1 to 4 carbon atoms, $R_1$ is methyl and $R_2$ is alkyl of about 4 to about 20 carbon atoms
so as to form an optically active bis (12-crown-4 methyl) dialkyl malonate enantiomer.

8. The method of claim 7 wherein X is Cl.

9. The method of claim 7 wherein X is $OR_3$.

10. The method of claims 8 or 9 wherein $R_2$ is dodecyl.

11. A method of preparing optically active bis (12-crown-4 methyl) dodecylmethyl malonate comprising reacting
a compound selected from
(S)(+)-hydroxymethyl 12-crown-4 and
(R)(−)-hydroxymethyl 12-crown-4 with
a compound having the general formula wherein X is Cl, OH or $OR_3$ and $R_3$ is lower alkyl of 1 to 4 carbon atoms
so as to form an optically active bis (12-crown-4 methyl) dodecylmethyl malonate enantiomer.

12. A method of preparing optically active bis (12-crown-4 methyl) dodecylmethyl malonate comprising reacting
a compound selected from
(S)(+)-hydroxymethyl 12-crown-4 and
(R)(−)-hydroxymethyl 12-crown-4 with
dodecylmethyl malonyl dichloride
so as to form an optically active bis (12-crown-4 methyl) dodecylmethyl enantiomer.

13. (S)(+)-hydroxymethyl 12-crown-4.

14. (R)(−)-hydroxymethyl 12-crown-4.

15. A method of preparing (S)(+)-hydroxymethyl 12-crown-4 comprising reacting (S)(+)-1,2-isopropylideneglycerol with allyl bromide to form (S)(+)-1-allyl-2,3-isopropylideneglycerol;

converting said (S)(+)-1-allyl-2,3-isopropylideneglycerol to (R)(+)-1-allylglycerol;

reacting said (R)(+)-1-allyl glycerol with bis-chloroethoxyethane to form (R)(+)-allyloxymethyl 12-crown-4;

converting said (R)(+)-allyloxylmethyl 12-crown-4 to (S)(+)-hydroxymethyl 12-crown-4.

16. A method of preparing (R)(−)-hydroxymethyl 12-crown-4 comprising reacting (R)(−)-1,2-isopropylideneglycerol with allyl bromide to form (R)(−)-1-allyl-2,3-isopropylideneglycerol;

converting said (R)(−)-1-allyl-2,3-isopropylideneglycerol to (S)(−)-1-allylglycerol;

reacting said (S)(−)-1-allyl glycerol with bis-chloroethoxyethane to form (S)(−)-allyloxymethyl 12-crown-4;

converting said (S)(−)-allyloxymethyl 12-crown-4 to (R)(−)-hydroxymethyl 12-crown-4.

* * * * *